United States Patent [19]

Aitchison et al.

[11] 4,141,809

[45] Feb. 27, 1979

[54] SEPARATION PROCESS

[75] Inventors: Gordon F. Aitchison, Abingdon; Patrick Mattock, Eynsham, both of England

[73] Assignee: United Kingdom Atomic Energy Authority, London, England

[21] Appl. No.: 929,681

[22] Filed: Jul. 31, 1978

[30] Foreign Application Priority Data

Aug. 17, 1977 [GB] United Kingdom ............ 34599/77

[51] Int. Cl.$^2$ ............................................. G01N 27/26
[52] U.S. Cl. ............................ 204/180 R; 204/299 R
[58] Field of Search ............... 204/180 R, 180 G, 299, 204/300

[56] References Cited

U.S. PATENT DOCUMENTS

| 2,648,636 | 8/1953 | Ellis et al. | 204/299 |
| 2,739,938 | 3/1956 | Wiechers | 204/301 |
| 3,197,394 | 7/1965 | McEuen | 204/180 R |
| 3,844,926 | 10/1974 | Smyth et al. | 204/299 |

Primary Examiner—Arthur C. Prescott
Attorney, Agent, or Firm—Larson, Taylor and Hinds

[57] ABSTRACT

Continuous flow electrophoresis in an apparatus such as described in U.S. Pat. No. 3,616,453 is stabilized by using a migrant solution containing a sufficient quantity of a liquid of density less than water such as ethanol. Continuous flow electrophoresis may be used, for example, in the fractionation and/or purification of a wide range of biologically active materials.

4 Claims, No Drawings

SEPARATION PROCESS

This invention relates to purification and/or separation by continuous flow electrophoresis.

The separation of proteins by continuous flow liquid electrophoresis has previously been described by Hannig (Z. Anal. Chem. 1961, 181, 244–254). Hannig describes injection of a thin stream of migrant solution into a thin film of buffer flowing laminarly between two thermostatically controlled and accurately spaced plates. An electric field is applied perpendicularly to the direction of flow of the film and parallel to the plates thereby to separate the components of the migrant into a number of bands dependent upon their electrophoretic mobilities. Hannig's process is, however, very difficult to scale-up, since the use of thicker films results in convection currents and consequent turbulent flow.

A further development in continuous flow electrohoresis is described in U.S. Pat. No. 3,616,453 where the stabilisation of flowing streams is effected by means of an angular velocity gradient. Thus, the separation is effected in an annular separation chamber defined between a central stationary cylinder (a stator) and an outer rotating cylinder (a rotor), which results in a gradient of angular velocity across the annular chamber giving stabilised laminar flow at much higher throughputs than can be achieved using the Hannig process mentioned above.

Examples of the application of the above processes are in the fractionation and/or purification of a wide range of biologically active materials, including macromolecules and sub-cellular particles.

In each of the known processes described above, a migrant solution is injected into a carrier flow stream. In the latter process, however, hydrodynamic instability may occur close to the point of injection thereby giving rise to a spread of migrant across the width of the annular chamber and introducing a constraint on throughput.

We have now found that this problem may be solved by reducing the density of the migrant solution.

Thus, the present invention provides a process for the purification and/or separation by continuous flow electrophoresis of an aqueous containing components of different electrophoretic mobilities, which comprises (i) injecting the solution, as a migrant solution, into a second aqueous solution, laminarly flowing in an annular separation chamber as a carrier solution for the migrant solution and stabilised by means of an angular velocity gradient, wherein the migrant solution contains sufficient water-miscible organic liquid of density less than 1 g ml$^{-1}$ at 20° C to reduce its density, relative to the density of the carrier solution, to a level such that injection of the migrant solution into the carrier solution does not give rise to hydrodynamic instability;

(ii) applying a constant electric field across the resulting mixture to produce a differential movement of the components of the migrant solution perpendicular to the direction of flow of the layer; and (iii) collecting desired separated components.

Thus, our invention is based upon the appreciation that the density differential between the migrant solution and the carrier solution is a contributory factor in causing the abovementioned hydrodynamic instability.

We have found that the use of the water-miscible organic liquid according to our invention may eliminate the hydrodynamic instability under conditions where it might otherwise occur and may greatly increase throughput. This will be illustrated in the examples below.

The organic liquid may be any water-miscible organic liquid of density less than 1 g ml$^{-1}$ provided that it meets the following requirements: it must not significantly affect the pH value of the migrant solution, it must not increase the electrical conductivity of the migrant solution, it must not cause deterioration in the materials from which the apparatus being used is constructed, and it must not degrade nor cause precipitation of migrant solution. Examples of such liquids, but conditional upon the above requirements are methanol and ethanol.

It should be noted that other factors may contribute to the abovementioned hydrodynamic instability. For example, the relative flow rates of migrant solution and carrier solution have been found to have an effect. Also, the rotation rate of the rotor (when a process as described in U.S. Pat. No. 3,616,453 is used) was found to have a positive second order effect on hydrodynamic stability except at small density differentials between migrant solution and carrier solution when its effect was very marked.

The present invention is applicable, for example, to a process as described in U.S. Pat. No. 3,616,453. In this case, the direction of migration of the migrant solution is centrifugal, hence the injection thereof is effected at the inner side of the flow of the carrier solution. Conveniently, the direction of flow is generally upward, and this is helical in pattern because of the effect of the rotation of the rotor.

The invention will now be particularly described, by way of example only, in Examples 1 to 3 below. Also included below is Example A which is a comparative example and is not an example of the invention.

EXAMPLE 1

A continuous electrophoretic separation apparatus of the type generally described in U.S. Pat. No. 3,844,926 was used. The apparatus had 29 outlet ports, a stator radius of 40 mm, a rotor radius of 45 mm to give an annular gap of 5 mm, and electrodes 304 mm in length.

An aqueous bovine serum albumin solution as migrant solution, to which had been added 12% (by volume) of ethanol was treated in the above apparatus using an aqueous triscitrate solution (pH 8.5, conductivity 1.0 mScm$^{-1}$ at 20° C) as carrier solution at a flow rate of 600 cm$^3$/minute. A product distribution with almost complete elimination of instability was obtained with a migrant solution flow rate of 17 cm$^3$/minute (i.e. 60 mg of bovine serum albimin cm$^{-3}$) which is a throughput of over 1 g/minute.

EXAMPLE A

By way of comparison and not as an example of the invention, the procedure of Example 1 was repeated under identical conditions but with the exception that the 12% (by volume) addition of ethanol was omitted. The maximum concentration of bovine serum albumin which could be obtained without instability was 25 mg cm$^{-3}$.

EXAMPLE 2

The procedure of Example 1 was repeated with the exception that an addition of 10% (by volume) of ethanol to the aqueous solution of bovine serum albumin was used. This was found to increase the standard deviation of the electrophoresed distribution by about 1% in comparison with Example A.

EXAMPLE 3

The procedure of Example 1 was repeated with the exception that an addition of 20% (by volume) of ethanol to the aqueous solution of bovine serum albumin was used. This was found to increase the standard deviation of the electrophoresed distribution by about 5% in comparison with Example A.

We claim:

1. A process for the purification and/or separation by continuous flow electrophoresis of an aqueous solution containing components of different electrophoretic mobilities, which comprises
   (i) injecting the solution, as a migrant solution, into a second aqueous solution, laminarly flowing in an annular separation chamber as a carrier solution for the migrant solution and stabilised by means of an angular velocity gradient, wherein the migrant solution contains sufficient water-miscible organic liquid of density less than $1 \text{ g ml}^{-1}$ at 20° C to reduce its density, relative to the density of the carrier solution, to a level such that injection of the migrant solution into the carrier solution does not give rise to hydrodynamic instability;
   (ii) applying a constant electric field across the resulting mixture to produce a differential movement of the components of the migrant solution perpendicular to the direction of flow of the layer; and
   (iii) collecting desired separated components.

2. A process according to claim 1 wherein the water-miscible organic liquid is methanol or ethanol.

3. A process according to claim 2 wherein the injection of the migrant solution is effected at the inner side of the flow of the carrier solution, and its direction of migration is centrifugal.

4. A process according to claim 3 wherein the flow is helical.

* * * * *